United States Patent [19]
Baerveldt et al.

[11] Patent Number: 5,476,445
[45] Date of Patent: Dec. 19, 1995

[54] GLAUCOMA IMPLANT WITH A TEMPORARY FLOW RESTRICTING SEAL

[75] Inventors: George Baerveldt, Shaker Heights, Ohio; Larry W. Blake, Coto de Caza, Calif.

[73] Assignee: Iovision, Inc., Irvine, Calif.

[21] Appl. No.: 283,961

[22] Filed: Aug. 1, 1994

Related U.S. Application Data

[63] Continuation-in-part of Ser. No. 917,575, Jul. 21, 1992, which is a continuation of Ser. No. 531,010, May 31, 1990, Pat. No. 5,178,604, and a continuation-in-part of Ser. No. 231,988, Apr. 21, 1994, Pat. No. 5,397,300, which is a continuation of Ser. No. 157,333, Nov. 23, 1993, abandoned, which is a continuation of Ser. No. 867,995, Apr. 13, 1992, abandoned, which is a continuation of Ser. No. 531,010, May 31, 1990, Pat. No. 5,178,607.

[51] Int. Cl.$^6$ .................................................. A61M 5/00
[52] U.S. Cl. .................................. 604/8; 604/9; 604/294; 604/50; 623/4
[58] Field of Search ........................... 604/8–10, 27, 604/30, 50, 43, 93, 128, 131, 149, 280, 294, 298; 623/4; 606/108

[56] References Cited

U.S. PATENT DOCUMENTS

| | | |
|---|---|---|
| 2,969,066 | 1/1961 | Holter et al. . |
| 3,109,429 | 11/1963 | Schwartz . |
| 3,159,161 | 12/1964 | Ness . |
| 3,527,226 | 9/1970 | Hakim . |

(List continued on next page.)

FOREIGN PATENT DOCUMENTS

| | | |
|---|---|---|
| 0102747 | 3/1984 | European Pat. Off. . |
| 0168201 | 1/1986 | European Pat. Off. . |
| 2233028 | 2/1975 | France . |
| 906561 | 2/1982 | U.S.S.R. . |
| 2101891 | 1/1983 | United Kingdom . |
| 2187963 | 9/1984 | United Kingdom . |
| 2160778 | 1/1986 | United Kingdom . |

OTHER PUBLICATIONS

Alder, Alder's Physiology of the Eye, "Intraocular Pressure", Chapter 5, pp. 249–277.

Bickford, "Molteno Implatn System", *Journal of Ophthalmic Nursing & Technology*, vol. 6, No. 6, pp. 224–229, 1987.

Davidovski, et al., "Long–Term Results with the White Glaucoma Pump–Shunt", *Ophthalmic Surgery*, vol. 21, No. 4, pp. 228–293, Apr. 1990.

Lee, et al., "Aqueous–Venous Shunt for Glaucoma", Surgical Techniques, *Arch Ophthalmol.*, vol. 99, pp. 2007–2012, Nov. 1981.

(List continued on next page.)

*Primary Examiner*—Mary Beth O. Jones
*Attorney, Agent, or Firm*—Knobbe, Martens, Olson & Bear

[57] ABSTRACT

An implant for use in the treatment of glaucoma is disclosed wherein the implant comprises an elastomeric plate having a non-valved elastomeric drainage tube attached thereto. The plate is curved so as to conform to the spherical anatomy of the eyeball. An annular sloped wall extends from the plate and surrounds the opening of the drainage tube into the plate. The plate is inserted beneath Tenon's capsule and sutured to the sclera utilizing temporary and non-dissolving permanent sutures. The annular wall provides a temporary sealing surface against the sclera. The drainage tube is tunnelled through the sclera and cornea and inserted into the anterior chamber, thus providing fluid communication between the anterior chamber and the elastomeric plate. The annular wall around the tube forms a temporary seal which restricts the drainage of aqueous fluid until formation of the bleb is completed. After bleb formation occurs, the temporary sutures around the wall are removed or dissolve. Once the temporary sutures are gone, the portion of the plate that is not stitched to the sclera floats within the bleb and breaks the seal between the implant and the sclera. Once the seal is broken, unrestricted flow between the anterior chamber and bleb is maintained.

17 Claims, 10 Drawing Sheets

U.S. PATENT DOCUMENTS

| | | |
|---|---|---|
| 3,788,327 | 1/1974 | Donowitz et al. . |
| 3,860,008 | 1/1975 | Miner et al. . |
| 3,915,172 | 10/1975 | Wichterle et al. . |
| 4,030,480 | 6/1977 | Meyer . |
| 4,240,434 | 12/1980 | Newkirk . |
| 4,373,218 | 2/1983 | Schackar . |
| 4,402,681 | 9/1983 | Haas et al. ................... 604/9 |
| 4,428,746 | 1/1984 | Mendez ....................... 604/8 |
| 4,521,210 | 6/1985 | Wong .......................... 604/8 |
| 4,722,724 | 2/1988 | Schocket ..................... 604/8 |
| 4,729,761 | 3/1988 | White .......................... 604/8 |
| 4,863,457 | 9/1989 | Lee . |
| 4,886,488 | 12/1989 | White .......................... 609/9 |
| 4,902,292 | 2/1990 | Joseph ......................... 623/4 |
| 4,915,684 | 4/1990 | MacKeen et al. ........... 604/8 |
| 4,936,825 | 6/1990 | Ungerleider ................. 604/8 |
| 4,946,436 | 8/1990 | Smith ........................... 604/8 |
| 4,968,296 | 11/1990 | Ritch et al. .................. 604/8 |
| 5,300,020 | 4/1994 | L'Esperance, Jr. .......... 604/9 |

OTHER PUBLICATIONS

Minckler, et al., "Clinical Experience with the Single–Plate Molteno Implant in Complicated Glaucomas", *Ophthalmology*, vol. 95, No. 9, pp. 1181–1188, Sep. 1988.

Molteno, "Use of Molteno Implants to Treat Secondary Glaucoma", *Glaucoma*, Grune & Stratton, Ltd., pp. 211–238.

"Experience with Molteno–Type Shunts", *Ocular Sugery News*, pp. 27–29, Jun. 1, 1989.

White, "A New Implantable Ocular Pressure Relief Device", University of South Dakota Medical School, Sioux Falls, South Dakota.

"Molteno™ Seton Implant For Management of Refractory Glaucoma", brochure distributed by Staar Surgical Company.

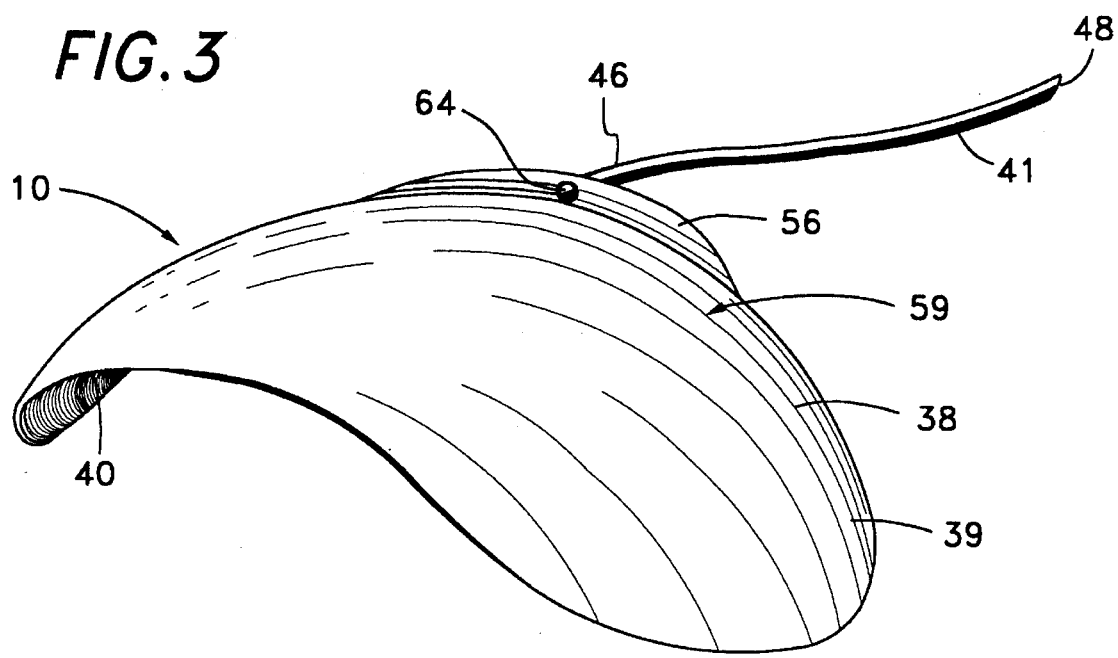
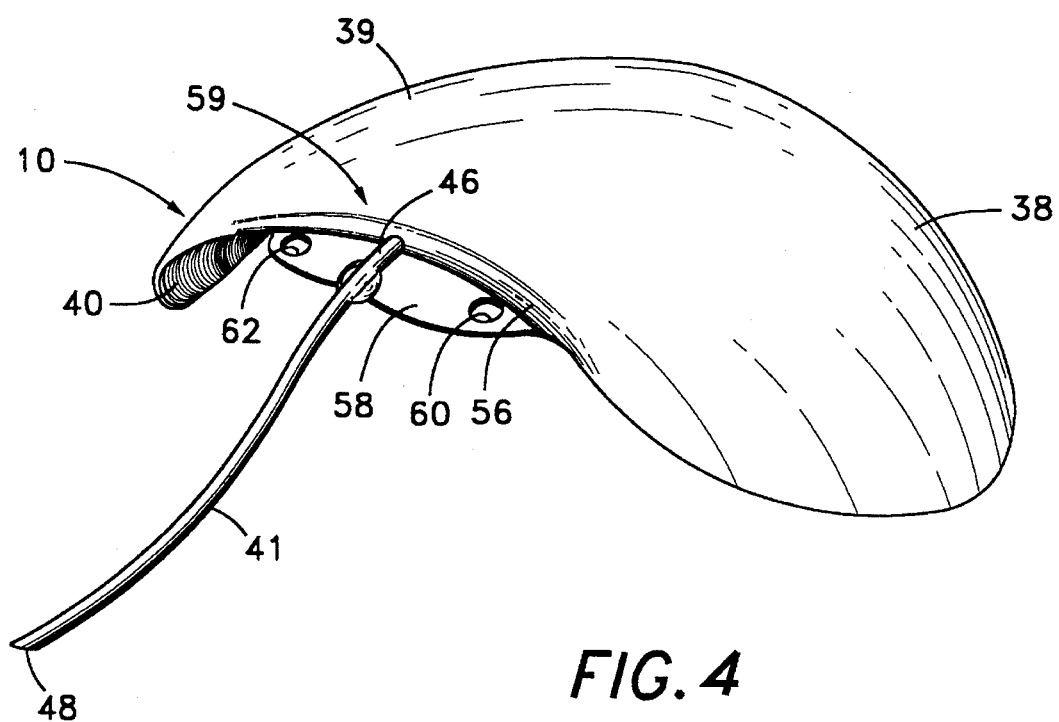

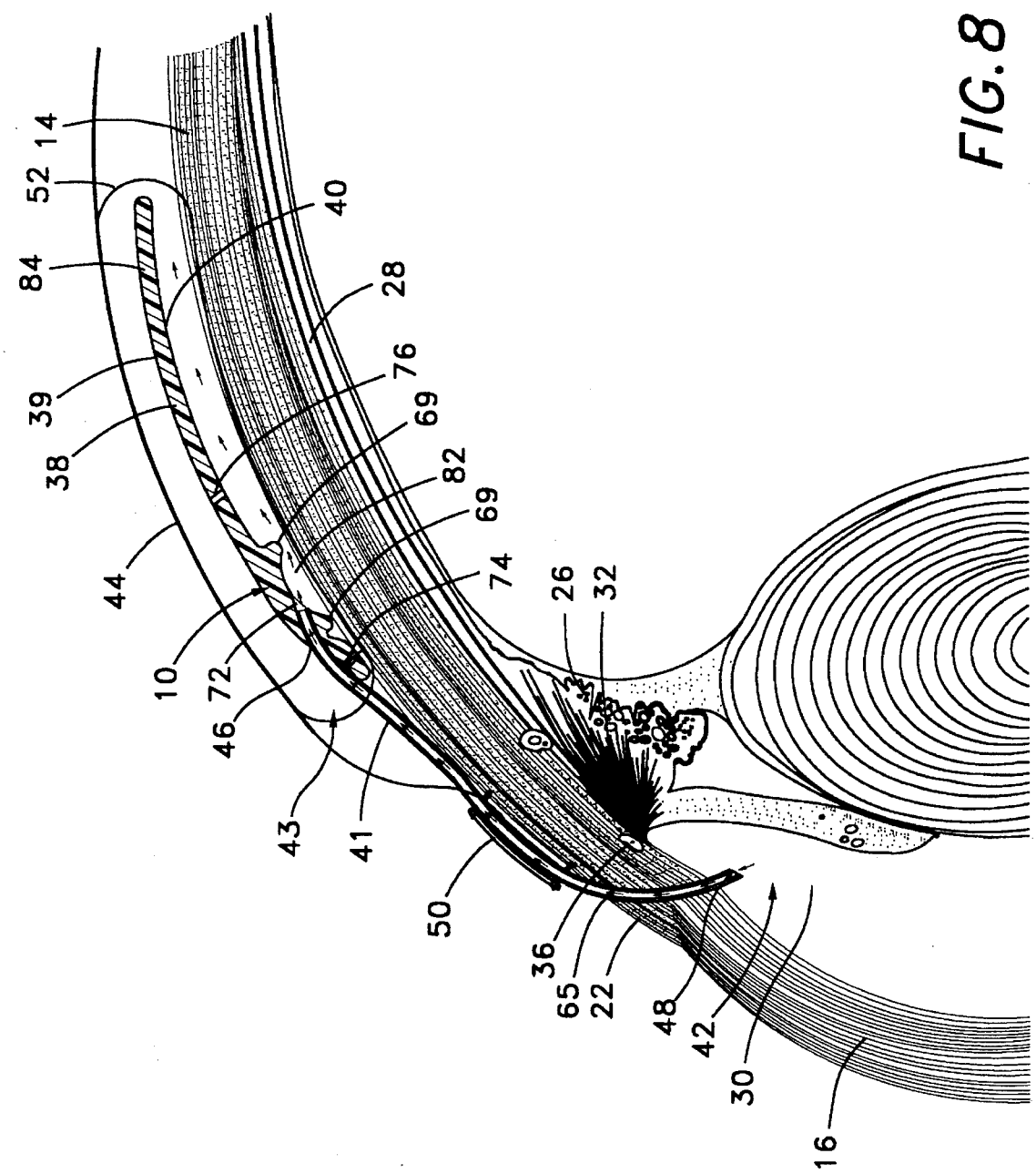

GLAUCOMA IMPLANT WITH A TEMPORARY FLOW RESTRICTING SEAL

RELATED APPLICATIONS

This application is a continuation-in-part of application Ser. No. 07/917,575 filed Jul. 21, 1992 which is a continuation of application Ser. No. 07/531,010 filed May 31, 1990, now issued as U.S. Pat. No. 5,178,604; and this application is also a continuation-in-part of application Ser. No. 08/231, 988 filed Apr. 21, 1994, now U.S. Pat. No. 5,397,300 which is a continuation of application Ser. No. 08/157,333 filed Nov. 23, 1993, now abandoned, which is a continuation of application Ser. No. 07/867,995 filed Apr. 13, 1992, now abandoned, which is a continuation in part of application Ser. No. 07/531,010 filed May 31, 1990, now issued as U.S. Pat. No. 5,178,604.

BACKGROUND OF THE INVENTION

1. Field of the Invention

The invention relates to ocular implants, and, in particular, to an implant used in the treatment of glaucoma.

2. Background

Intraocular pressure in the eye is maintained by the formation and drainage of aqueous, a clear, colorless fluid that fills the anterior and posterior chambers of the eye. Aqueous normally flows from the anterior chamber of the eye out through an aqueous outflow channel at a rate of 2 to 5 microliters per minute.

Glaucoma is a progressive disease of the eye characterized by a gradual increase of intraocular pressure. This increase in pressure is most commonly caused by stenosis or blockage of the aqueous outflow channel, resulting in excessive buildup of aqueous fluid in the eyeball. Other causes include increase in venous pressure outside the eye which is reflected back through the aqueous drainage channels and increased production of aqueous. In a "normal" eye, intraocular pressure ranges from 8 to 21 mm mercury. In an eye with glaucoma, this pressure can range between the so called normal pressures and pressures up to as much as 50 mm mercury. This increase in intraocular pressure produces gradual and permanent loss of vision in the afflicted eye.

Existing corrective methods for the treatment of glaucoma include drugs, surgery, and implants. Pharmacological treatment is prohibitively expensive to a large majority of glaucoma patients. In addition, many people afflicted with the disease live in remote or undeveloped retirement areas where the drugs are not readily accessible. The drugs used in the treatment, in particular steroids, often have undesirable side effects and many of the long-term effects resulting from prolonged use are not yet known.

Surgical procedures have been developed in an effort to treat victims of glaucoma. An iridectomy, removal of a portion of the iris, is often used in angle-closure glaucoma wherein there is an occlusion of the trabecular meshwork by iris contact. Removal of a piece of the iris then gives the aqueous free passage from the posterior to the anterior chambers in the eye. A trabeculotomy, opening the inner wall of Schlemm's canal, is often performed in cases of developmental or juvenile glaucoma so as to increase the outflow of the aqueous, thereby decreasing intraocular pressure. In adults, a trabeculotomy shunts fluid through a trap-door flap in the eye that performs a valve-like function for the first few weeks after surgery. While often successful, these surgical techniques possess inherent risks associated with invasive surgery on an already afflicted eye. Furthermore, the tissue of the eye can scar over this small area and the eye reverts to the pre-operative condition, thereby necessitating the need for further treatment.

Ocular implants are often used in long-term glaucoma treatment. One such implant is disclosed in U.S. Pat. No. 4,457,757 entitled "Device for Draining Aqueous Humor" and commercially available as the Molteno™ Seton Implant. The implant comprises a drainage tube connected to one or more rigid plate reservoirs. The reservoir plates conform to the curvature of the eye. A reservoir plate is placed under Tenon's capsule and sutured to the sclera.

The drainage tube is implanted into the anterior chamber through a scleral flap. A second plate can be passed under the superior rectus muscle and sutured to the sclera. At this point, the body will form scar tissue around these plates. Increased pressure causes the tissues above the plates to lift and form a bleb into which aqueous flows from the anterior chamber drains via the drainage tube. This type of implant is disadvantageous as the plates are formed of a rigid plastic which makes insertion beneath the eye tissue difficult and time-consuming.

UK Patent Application 2,160,778 entitled "Aqueous humor drainage device" discloses a similar type of implant device comprising a drainage tube and a drainage body. The tube is fixed to and opens directly onto a surface of the body. The device is sutured to the sclera of the eye and the tube positioned within the anterior chamber to provide outflow for the aqueous contained therein. The device further includes a pressure gradient limiting valve formed as a slit in the tube. However, when the device is implanted in the eye and is surrounded by aqueous humor, an extremely small flow rate of aqueous humor will pass through the slit, thus the slit in the tube functions not as a valve but as a flow restrictor. This type of device does not allow patent, i.e., open or two-way, flow through the drainage tube, and prevents retrograde aqueous flow into the anterior chamber. This device is considered a valved glaucoma implant because it has a permanent structure in the flow path obstructing the flow of aqueous from the anterior chamber. A non-valved device has a patent uninterrupted flow of aqueous to and from the anterior chamber, i.e., the implant has no permanent structure in the fluid flow path which obstructs the flow of the aqueous.

During the first few days after surgery and before scar tissue forms a bleb around the glaucoma implant device, it is possible for too much fluid to flow from the eye and create an extremely low to zero pressure in the eye. This low pressure could cause the eye to collapse and cause considerable and often permanent damage to the eye. It is desirable to provide a sealing mechanism that would prevent this pressure drop during the initial stages of the bleb formation and would enable a greater pressure release once the bleb has formed. Actual experience has shown that it is often necessary to apply a "purse-string" suture around the drainage tube which occludes drainage flow until the bleb has formed. Generally, the scar formation requires up to 8 weeks. After the scar is formed, the suture dissolves, but occasionally a second surgical procedure is necessary to cut the suture.

U.S. Pat. No. 4,750,901 issued to Molteno discloses a glaucoma implant with an elevated peripheral ridge, a subsidiary elevated ridge on the upper surface of the implant and a drainage tube which leads from the upper surface of the plate to the anterior chamber of the eye. The Molteno patent discloses that the tube enters the peripheral ridge to a position above the upper surface of the plate and the subsidiary ridge is located around the entrance of the tube. The subsidiary ridge is forced against Tenon's tissue, i.e., Tenon's capsule, to create an initial bleb cavity much smaller in area than the total bleb cavity. The Molteno patent discloses that the addition of the subsidiary ridge to the upper surface of the plate around the exit of the tube has the effect of providing a pressure sensitive one-way valve effect. The Molteno patent also discloses that, once the eye recovers from the operation, the increased production of the aqueous fluid by the eye raises the pressure in the eye and also within the small bleb cavity causing the overlying Tenon's capsule to be lifted slightly thereby allowing fluid to gain access to the entire bleb cavity.

In practice however, the Molteno device fails to provide an effective sealing surface with Tenon's capsule and the desired one-way valve effect does not occur. The main reason that the Molteno device is not functional as a one-way valve is that the tissue of Tenon's Capsule stretches so that there is little pressure against the subsidiary ridge to provide a sealed valve surface. In addition, Tenon's capsule is a thin layer of tissue and theoretically can only maintain the orbital tissue pressure of approximately 0 to 2 mm mercury to form a seal against the ridge on the implant. The orbital tissue pressure can not maintain the pressure within the eye of between 4 to 12 mm mercury for a normal eye and up to 20 mm mercury for patients that have severe glaucoma with the seal against the subsidiary ridge on the Molteno implant. Further, the tissue of Tenon's capsule is thin and has greater fluid permeability than other tissues in the eye, such as the sclera or conjunctiva, and undesired fluid flow passes though the tissue of Tenon's capsule. These forces alone or in combination are stronger than the weak seal provided by the Molteno device and the Molteno device cannot form a sufficient seal to create the desired one-way valve. Instead, the Molteno subsidiary ridge allows fluid to flow around it and advances almost directly into the full sized bleb. Thus, the Molteno device is not effective in preventing an initial large pressure drop in the eye in most cases and post-operative hypotony ensues.

Therefore, it would be desirable to provide a non-valved glaucoma implant device which results in a temporary flow restriction of fluid from exiting the anterior chamber of the eye and after sufficient time has elapsed creates a patent flow of fluid to/from the anterior chamber of the eye without requiring a second surgical operation.

SUMMARY OF THE INVENTION

The present invention provides an implant for the treatment of glaucoma which creates a temporary seal to restrict the flow of fluid from the anterior chamber of the eye and after a period of time provides unrestricted flow between the implant and the anterior chamber of the eye. The implant comprises a single plate formed of a pliable, elastomeric material having a non-valved tube attached to and opening onto a surface of the plate. The plate is sutured to the scleral tissue at the forward portion of the plate utilizing permanent sutures to keep the plate from migrating and impinging on the eye socket tissue or extruding from the eye tissue. The plate is covered by a thick flap of Tenon's capsule to be encapsulated within a drainage bleb. The attached tube is tunneled through the sclera and the cornea and positioned within the anterior chamber to provide a drain for aqueous fluid. Because of the pliable construction, the device can be implanted with greater ease than previous implants. This substantially shortens the time required to perform the surgical procedure and to implant such large surface area implants.

In a unique aspect of the invention, an annular sloped wall surrounds the opening of the tube onto the carrier plate. The wall provides a sealing surface against the sclera which is similar to an o-ring seal. The pliable plate is sutured to the sclera utilizing temporary sutures equally spaced around the annular wall to provide and enhance the seal of the wall against the sclera. The sutures in the plate force the plate and wall against a small area of sclera causing a mechanical seal that allows pressure to build up in the reservoir formed by the o-ring configuration of the wall and the tube and the anterior chamber of the eye. When the pressure in this system is greater than the sutures placed against the sclera, the fluid will flow between the surface of the plate and the sclera thus maintaining a constant pressure within the eye. The wall around the tube forms a temporary seal that allows the fluid to escape. Once the pressure in the tube and thus the eye exceeds the pressure established by the sutures, drainage of fluid into the periorbital tissues is permitted. Once the bleb formation occurs, the temporary sutures around the seal are dissolved, absorbed or are removed. After the sutures are gone, the plate floats within the bleb, breaks the seal between the wall and the sclera, and allows unrestricted flow between the anterior chamber and the entire bleb.

BRIEF DESCRIPTION OF THE DRAWINGS

FIG. 3 shows a first perspective view of the implant of the present invention;

FIG. 4 shows a second perspective view of the implant of the present invention;

FIG. 8 is a cross-sectional view of the implant of FIG. 5 and FIG. 6 implanted in the eye after bleb formation occurs;

DETAILED DESCRIPTION OF THE INVENTION

Figure 1:
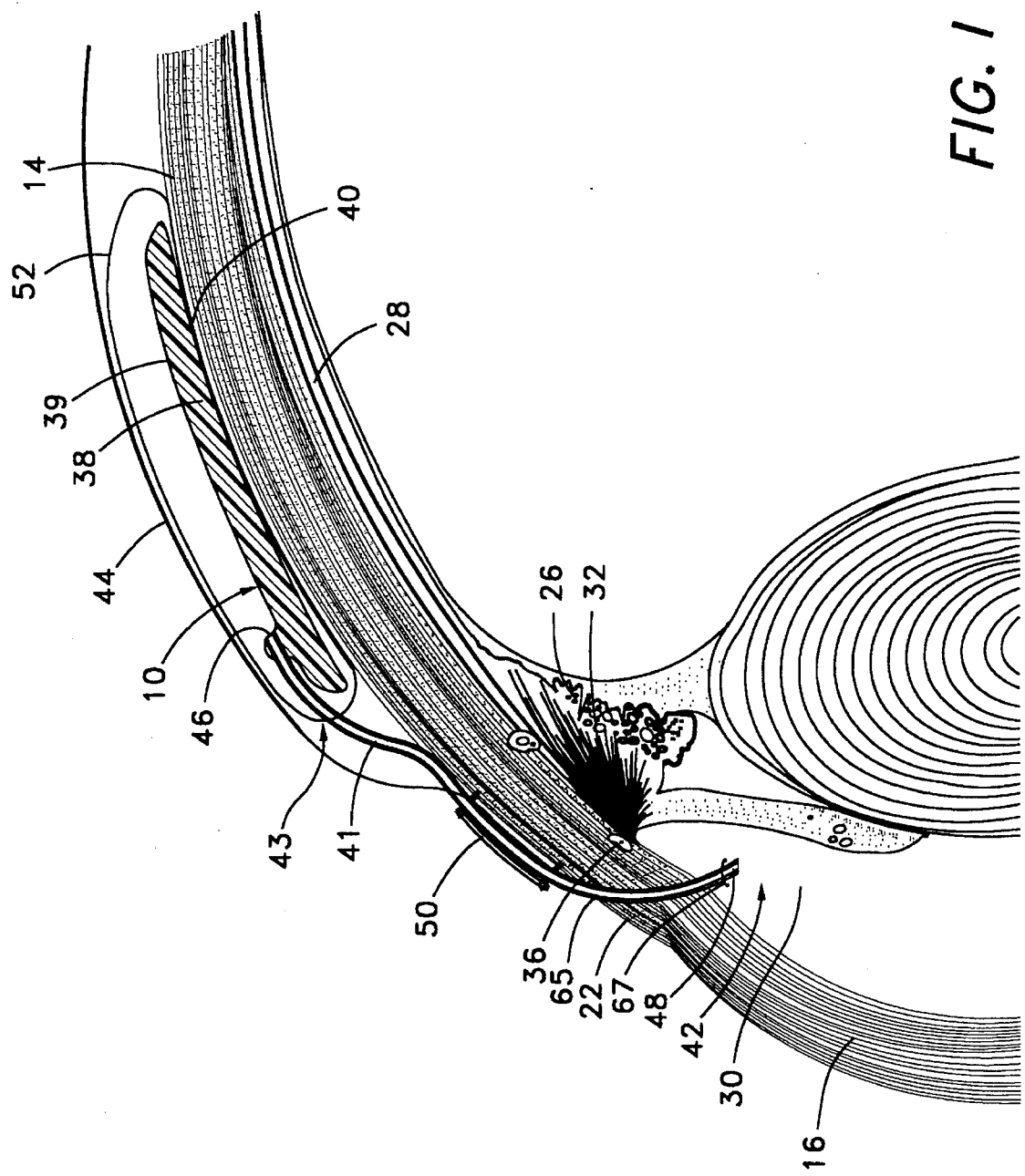
FIG. 1 shows a cross section which illustrates the implant of the present invention in a human eye.
Figure 2:
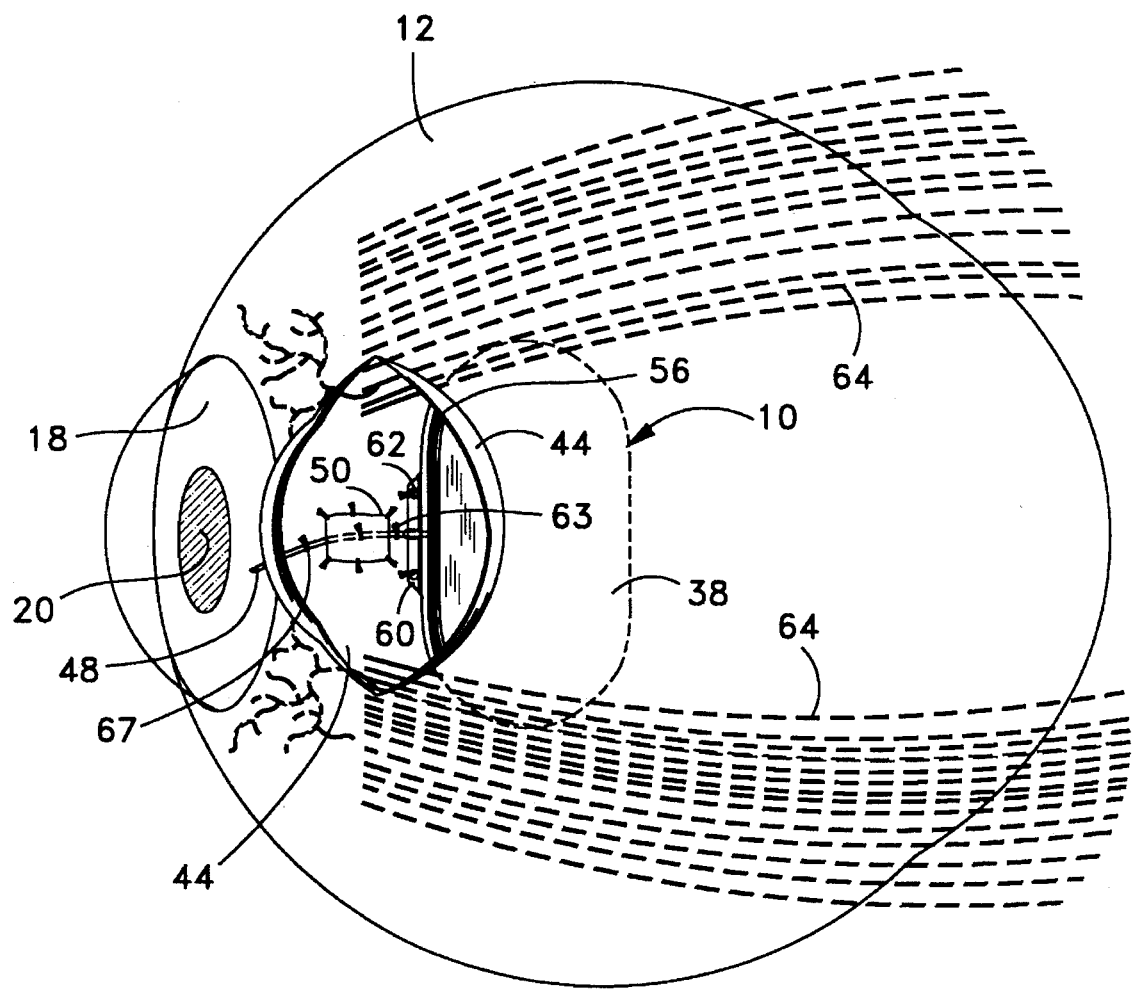
FIG. 2 shows a cut-away view of the implant of the present invention in a human eye.

FIG. 1 and FIG. 2 illustrate an implant 10 constructed in accordance with the present invention positioned within the tissue of an eye 12. The relevant structure of the eye 12 will be described briefly below to provide background for the anatomical terms incorporated herein, however, it should be realized that several anatomical details have been omitted for clarity of understanding. The tough outer membrane known as the sclera 14 covers all of the eye 12 except that portion covered by the cornea 16, the thin, transparent membrane which covers the iris 18 and the pupil 20. The cornea 16 merges into the sclera 14 at a juncture referred to as the sulcus of the sclera or as the limbus 22. The ciliary body 26 begins at the limbus 22 and extends along the interior of the sclera 14 and becomes the choroid 28. The choroid 28 is a brown vascular membrane which extends along the retina back toward the optic nerve.

It is well-known that aqueous is produced by the ciliary body 26 and reaches the anterior chamber 30 formed between the iris 18 and the cornea 16 through the pupil 20. In a normal eye, the aqueous is removed through the trabecular meshwork 32. There the aqueous passes through Schlemm's canal 36 and through veins which merge with blood-carrying veins and into venous circulation. Intraocular pressure is maintained in the eye 12 by the intricate balance of secretion and absorption or outflow of the aqueous in the manner described above. Glaucoma results from excessive buildup of aqueous fluid in the anterior chamber 30 which produces an increase in intraocular pressure.

The present invention is designed for treatment of glaucoma by facilitating the outflow of the aqueous from the anterior chamber 30 of the eye 12. The implant 10 comprises a pliable plate 38, also referred to as a pliable seton in the ophthalmic field, having oppositely disposed first 39 and second 40 curved surfaces, connected to a drainage tube 41 which extends into a first region 42 of the eye 12. As illustrated in FIG. 1, the seton 38 is implanted in a second region 43 of the eye 12 beneath a layer of Tenon's capsule 44 mid sutured to the sclera 14. The discharge tube 41 comprises a first end 46 and a second end 48 wherein the first end 46 is attached to the plate 38 adjacent the first surface 39 of the plate 38. The second end 48 of the tube 41 extends through the layer of Tenon's capsule 44 and through the cornea 16 into a first region 42 of the eye 12 such as the anterior chamber 30 of the eye 12, to provide fluid communication between the first region 42 and the second region 43 of the eye 12. A scleral reinforcing element 50, such as a connective tissue graft, i.e., a sclera graft, dura mater graft, fascia lata graft, or a graft formed from other biocompatible materials, covers the exposed portion of the tube 41 located between the Tenon's capsule 44 and the sclera 14 and the cornea 16. A large drainage bleb 52 surrounds the seton 38 and lifts the layer of Tenon's capsule 44 above the sclera 14. The seton acts as a permanent bleb controlling stent to inhibit the tendency of the body to heal itself which would eliminate the bleb.

The implant 10 is shown in more detail in FIG. 3 and FIG. 4. The plate 38 is generally spherical in shape and has a perimeter which is elliptical. The surface area of the plate 38 is preferably in the range of approximately 100 to 600 mm$^2$ depending on glaucoma conditions and the radius of curvature of the plate 38 is preferably 12 to 14 mm. The plate 38 includes a raised ridge 56 formed adjacent one of the larger-radius perimeter edges of the plate 38, on the first curved spherical surface 39 of the plate 38. The rounded edge of the plate 38 extending on either side of the raised ridge 56, not including that portion of the plate 38 adjacent the ridge 56, is entirely radiused, tapered and blended so as to facilitate insertion as described below. Additionally, the rounded edge of the plate 38 is tapered and blended to discourage the unwanted growth of scar tissue on the plate 38 which may lock the plate 38 into an unwanted position. The rounded edge of the plate 38 provides a smooth surface from which the scar tissue preferably slides off and is therefore unable to completely anchor onto the plate 38. The second surface 40 of the plate 38 is curved to conform to the curvature of the eye 12 and the curvature of the ridge 56 matches the curvature of the sclera 14. An extension 58 of the plate 38 is formed adjacent the ridge 56 in the plate 38 and includes two small suture holes 60, 62. The thickness of the plate 38 is preferably in the range of 0.5 to 2.0 mm.

The drainage tube 41 is connected to the plate 38 with adhesive, such as Clear Silicone Rubber Adhesive RTV-118 manufactured by General Electric Silicone Products of Waterford, N.Y., via a small hole 64 formed in the ridge 56 and is bonded to the plate 38 using well-known bonding techniques. The first end 46 of the tube 41 thus drains into the recess formed at the junction of the ridge 56 and the smooth first surface 39 of the plate 38. The plate 38 is preferably formed of silicone elastomer, such as SILASTIC™, Medical Grade Q7-4765, 65 Shore A, manufactured by Dow Corning Corporation of Midland, Mich. or Nusil Corp. of Santa Barbara, Calif., although other silicone elastomers in the range of 40–85 Shore A and having good elastic memory are also suitable. The silicone elastomer is filled with a radiopaque material, such as Barium Sulfate, so that the implant is visible in X-rays procedures, thereby allowing patient progress monitoring. The drainage tube 41 is preferably a 1.0 to 3.0 French flow tube, approximately 10 mm to 15 mm in length, formed of SILASTIC™, Medical Grade RX-50, also available from Dow Corning Corporation or Nusil Corp. of Santa Barbara.

The present invention can be implanted using known ophthalmological surgical techniques and, with reference to FIG. 1, FIG. 2 and FIG. 4, the surgical implant procedure will be briefly described. An initial incision 63 is made in the Tenon's capsule 44 parallel to the limbus 22. The plate 38 is inserted into the second region 43 of the eye 12 through the initial incision 65 and positioned beneath the Tenon's capsule 44 and a portion of the rectus muscle 64 or extending totally under one or more muscles, thus covering the sclera 14. The plate 38 can be sutured to the sclera 14, or alternatively, to the rectus muscle 64 if the sclera 14 is thinned by disease, with the suture holes 60, 62. Preferably, nonabsorbable nylon sutures are used in the suture holes 60, 62 to secure the plate 38, such as 8-O nylon or polypropylene sutures. The drainage tube 41 is tunneled out through the sclera 14 and the cornea 16 beneath Tenon's capsule 44 and in through an incision 65 in the region of the limbus 22 such that the second end 48 of the tube 41 extends into a first region 42, such as the anterior chamber 30, of the eye 12. The exposed portion of the drainage tube 41 is then covered with a scleral reinforcing element 50. In one embodiment, the drainage tube 41 is sutured closed with a temporary suture(s) 63, 67 at a location on either side of the sclera reinforcing element 50 to prevent any drainage of aqueous prior to formation of the bleb tissue 52 over the plate 38. In actual practice, it has been found that initially after surgery aqueous fluid will weep through a space formed between the yet to be healed incision 65 and the drainage tube 41. This weeping of the aqueous fluid through the incision 73 relieves some of the fluid pressure until the bleb 52 has formed and the temporary suture(s) 63, 67 is/are removed or absorbed by the body. In one embodiment, the temporary suture(s) 63 is a dissolvable suture while suture 67 is nonabsorbable. In an alternate, but not preferred, embodiment, the temporary sutures 63, 67 are removed during a secondary procedure, such as a surgical procedure or an ophthalmic laser procedure. Both procedures are known to those of skill in the art.

The formation of the bleb 52 occurs in response to the introduction of the plate 38 into the tissue of the second region 43 of the eye 12. The bleb 52 comprises a thin layer of connective tissue which encapsulates the plate 38, and substantially all of the surfaces of the plate 38 contact the tissues in the second region 43 of the eye 12, thus lifting the Tenon's capsule 44 above the sclera 14 as shown. Typically, bleb 52 formation occurs in the range of 1 to 8 weeks postoperatively. In the above embodiment, an additional surgery can be performed at this time to remove the suture(s) 63, 67 from the drainage tube 41 and allow flow of aqueous from the anterior chamber 30 to the bleb 52 via the drainage tube 41. Alternatively, a dissolving suture can be used to seal the drainage tube 41. After removal or dissolution of the suture(s) 63, 67 blocking the drainage tube 41, the aqueous flow between the tube 41 and bleb 52 is advantageously a patent flow, allowing both flow from the anterior chamber 30 to the bleb 52 and vice versa. This ensures that retrograde non-valved flow from the bleb 52 to the anterior chamber 30, occurring in response to pressure on the eye 12 from the outside, for example, when the lid is forced closed or when the eyeball is pressed on with a finger, does not adversely or harmfully affect intraocular pressure within the eye 12. The fluid contained in the bleb 52 seeps through the bleb into intercellular spaces within the eye 12 and is then removed through surrounding capillaries or lymphatics.

The flexible elastomeric material used to form of the present invention, and the size and elliptical shape of the plate 38 allows the implant 10 to be inserted much more easily than previously realized with other glaucoma treatment implants. During the insertion process, the plate 38 can be "folded" in half about the axis of the tube 41 and then inserted through the incision 63. Once placed through the incision 63, the plate 38 will return to its original shape and can be positioned to cover the sclera 14, as described above. Further, the flexible material from which the plate 38 is formed is soft and pliable which results in much less trauma and irritation to the surrounding tissues and vasculature than experienced with a rigid plate device. In addition, since the plate 38 can be folded, a smaller incision can be made in the Tenon's capsule 44. Thus, the pliable plate 38 significantly decreases the surgical procedure length while also minimizing tissue and vasculature damage which can occur in the insertion process.

Figure 5:
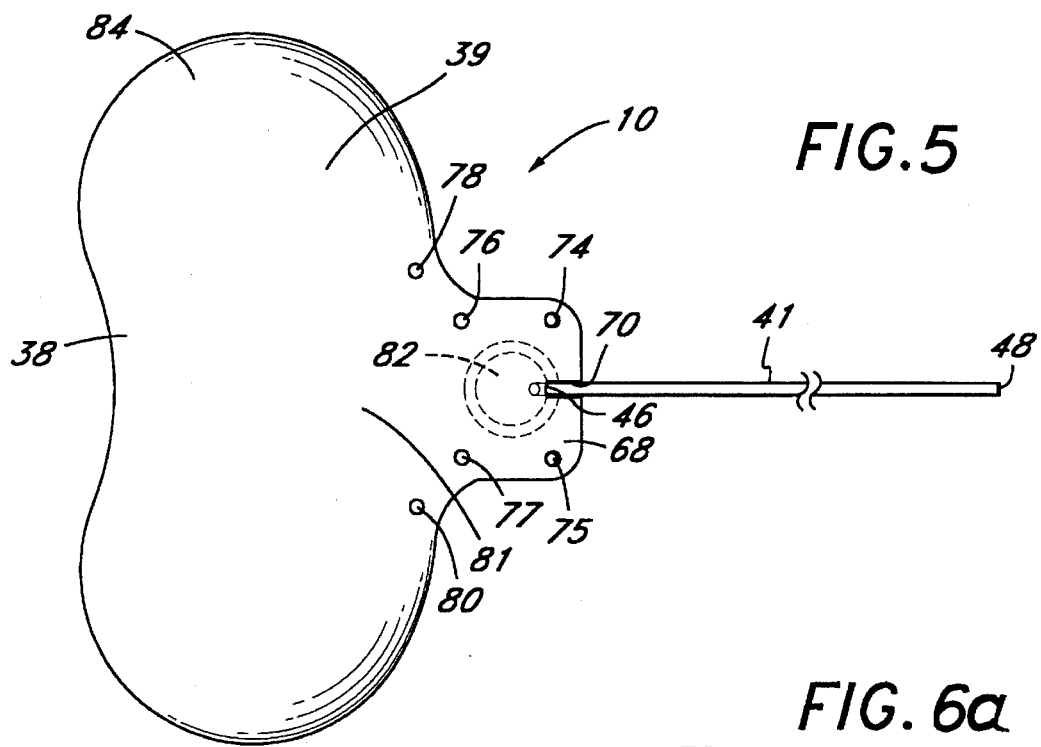
FIG. 5 is a top plan view illustrating the preferred embodiment of the implant.
Figure 6A:
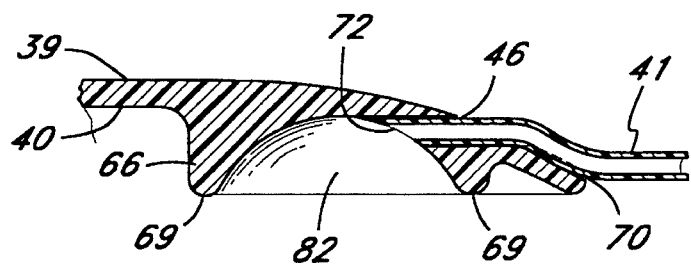
FIG. 6a is a cross-sectional view showing the line 6a—6a of FIG. 6.
Figure 6:
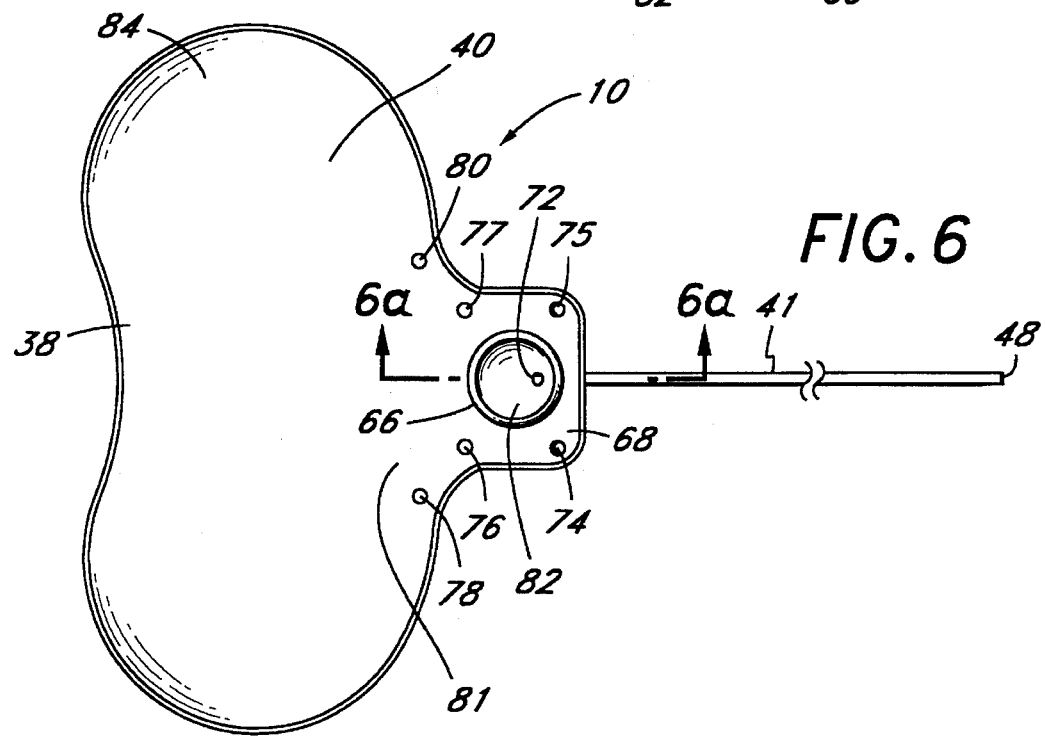
FIG. 6 is a bottom plan view illustrating the preferred embodiment of the implant.

In the preferred embodiment of the implant 10 illustrated in FIG. 5, FIG. 6 and FIG. 6a, the plate 38 has a profile shape that is generally spherical and conforms to the contour of the eye. Preferably, the plate 38 is shaped like the profile of an elongated soybean. The soybean shape is similar to the elliptical shape of FIG. 3 and FIG. 4 with a rearward portion of the plate 38 removed. The soybean shape is preferred as the removed rearward portion of the plate 38 prevents the plate 38 from interfering with the optic nerve. As indicated above, the surface area of the plate 38 is preferably in the range of approximately 100 to 600 mm$^2$ depending on glaucoma conditions. A sloped wall 66 extends from the second surface 40 of the plate 38 in a forward portion 68 of the plate 38. The dimensions of the forward portion 68 of the plate 38 in which the sloped wall 66 extends is from 2 to 20 mm in length and from 2 to 20 mm in width. In the preferred embodiment, the dimensions of the forward portion 68 of the plate are 6 mm in length and 4 mm in width. The dimension of the forward portion 68 of the plate 38 could be larger or smaller than those described above to accommodate a cavity 82 of the desired dimensions. Preferably, the sloped wall 66 has a blended and rounded edge to provide a smooth surface from which scar tissue preferably slides off instead of connecting to the wall 66. Desirably, the sloped, blended rounded edge of the wall 66 prevents scar tissue from anchoring onto the implant 10 and permanently tethering the plate 38 to the sclera in an undesired position. The sloped wall 66 is preferably 25 microns to 5 mm thick, i.e., wide and 50 microns to 4 mm in height. The tip of the sloped wall 66 forms a sealing surface 69 which seals against the sclera 14 upon implantation.

The drainage tube 41 is connected to the plate 38 of the preferred embodiment along a first notch 70 formed in the first surface 39 of the plate 38, and then through an opening or small hole 72 formed in the plate 38 which opens into the second surface 40 of the plate 38. The first end 46 of the tube 41 is bonded to the plate 38 along the notch 70 with adhesive, as described above, and using well-known bonding techniques. The tube 41 is bonded to the hole 72 in the plate 38 such that the first end 46 of the tube 41 is open to the second surface 40 of the plate 38.

The sloped wall 66 completely surrounds the opening 72 in the second surface 40 of the plate 38. Preferably, the sloped wall 66 surrounds an area of approximately 0.08 mm$^2$–75 mm$^2$ around the opening 72 in the second surface 40 of the plate 38. More preferably, the sloped wall 66 surrounds an area of approximately 2 mm$^2$–14 mm$^2$ around the opening 72 in the second surface 40 of the plate 38. In the preferred embodiment, the sloped wall 66 is annular in shape to evenly surround the opening 72 and the diameter of the annular shape covered by the wall is preferably between approximately 1 mm to 4 ram, but could be as large as 15 mm. In the preferred embodiment, the annular sloped wall forms a concave cupped cavity 82 as defined by the sloped wall 66 and the second surface 40 of the plate 38. As will be recognized by one of skill in the art, the sloped wall 66 may take on a variety of shapes, such as oval, heart shaped, square, rectangular, triangular, etc., in most cases the shape surrounds the opening 72 in the second surface 40 of the plate 38. A first plurality of suture holes 74–77 are provided around the sloped wall 66. In the preferred embodiment, the first plurality of sutures holes 74–77 are evenly spaced around the perimeter of the forward portion 68 of the plate 38. A second plurality of suture holes 78, 80 are provided in an intermediate 7 portion 81, proximal to the forward portion 68, of the plate 38 to enable a surgeon to further secure the plate 38 to the sclera 14 (FIG. 7).

Figure 7:
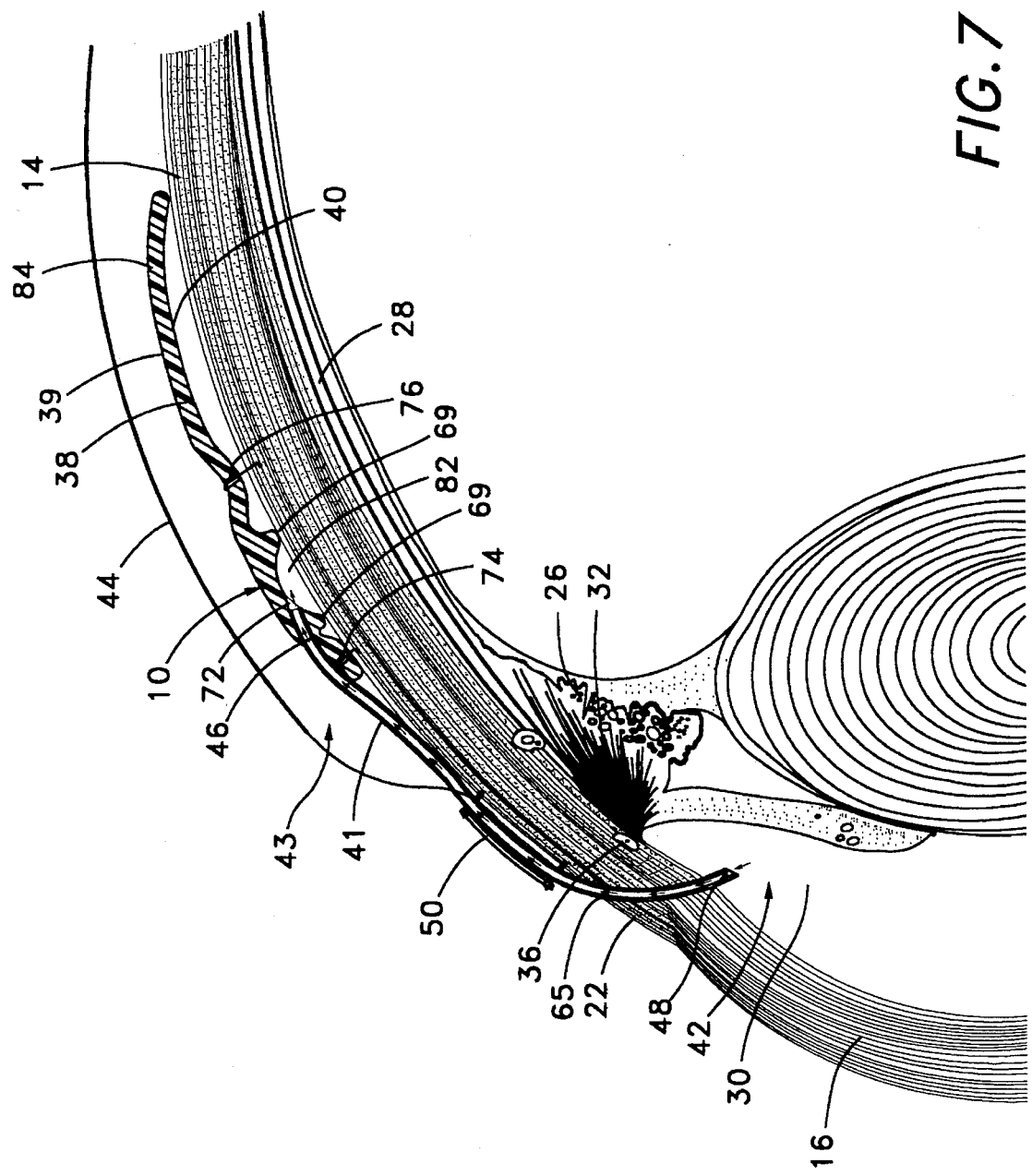
FIG. 7 is a cross-sectional view of the implant of FIG. 5 and FIG. 6 implanted in the eye immediately after surgery.

Referring also to FIG. 7, when the implant 10 of the preferred embodiment is inserted into the eye 12, utilizing the procedure described above, the plate 38 is inserted into the second region 43 of the eye and positioned beneath the Tenon's capsule 44 and a portion of the rectus muscle (FIG. 2), thus covering the sclera 14. The tip of the sloped wall 66 creates a sealing surface 69 against the sclera 14. Preferably, the seal is similar to an o-ring seal. By positioning the implant 10 such that the rectus muscle is covering a portion of the implant 10, the rectus muscle helps hold the implant 10 against the sclera 14 but does not create any portion of the desired seal. The implant 10 lies between the sclera 14 and Tenon's capsule 44. Tenon's Capsule 44 lies on the upper surface 39 of the plate 38, but Tenon's Capsule 44 does not create a portion of the desired seal. During implantation, the plate 38 is sutured to the sclera 14 utilizing both absorbable and nonabsorbable sutures in a first plurality of suture holes 74–77 and absorbable or nonabsorbable sutures in a second plurality of suture holes 78, 80. The first plurality of suture holes 74–77 are spaced around the sloped wall 66 to provide an enhanced seal of the wall 66 against the sclera 14. The second plurality of sutures 78,80 on the immediate portion 81 of the plate 38 assist in tethering the plate 38 to the sclera 14. After implantation, the aqueous fluid from the first region 42 of the eye 12 drains through the drainage tube 41 into the concave cupped cavity 82 which is sealed against the sclera 14. The sutures 74–77 assist in sealing the cupped cavity 82 against the sclera 14 at the sealing surface 69; therefore, the aqueous fluid is unable to escape from the cavity 82. Once the cavity 82 is filled with fluid, the fluid pressure within the sealed cavity 82 prevents additional fluid from draining from the first region 42 of the eye 12 into the cavity 82, thereby preventing low pressure from occurring in the second region 42 of the eye 12. As will be recognized by those of skill in the art, the dimensions of the cavity 82 are selected to define the flow of fluid that can exit the first region 42 of the eye 12, before the flow is restricted, without creating a pressure drop in the eye 12. Therefore, the sealing of the wall 66 of the plate 38 against the sclera 14 creates a sealed cavity 82 which temporarily occludes the drainage of aqueous fluid from the first region 42 of the eye 12. This o-ring seal effect is achieved both by the design of the implant 10 and the tension produced by the absorbable and nonabsorbable sutures placed by the surgeon in the first plurality of suture holes 74–77 and/or the second plurality of suture holes 78, 80. The sutures hold the implant 10 against the sclera 14 with the necessary tension desired by the surgeon. In a preferred embodiment, the tension level of the sutures is set to withstand pressures of up to 10–20 mm mercury. Preferably, the fluid pressure in the first region 42 of the eye 12 reaches an equilibrium pressure with the pressure in the cavity 82 while scar tissue in the eye forms a bleb 52. This equilibrium pressure is less than the pressure applied by the sutures. Further, some fluid in the cavity 82 may be absorbed by the sclera tissue below the cavity 82. This absorption of fluid will help maintain the desired equilibrium pressure. When the pressure in the cavity 82 and the first region 42 of the eye 12 exceed the tension of the sutures as applied by the surgeon, fluid will leak around the o-ring seal and maintain the eye pressure determined by the surgeon. This prevents the eye pressure from exceeding a specific value, as determined by the tension of the sutures as applied by the surgeon, which could cause damage to the eye. If the fluid pressure does not exceed the tension of the sutures, the o-ring type seal will maintain the fluid pressure within the cavity 82.

In the preferred embodiment, the temporary sutures are dissolvable sutures. In an alternate, but not preferred embodiment, the temporary sutures ewe removed during a secondary procedure, such as a surgical procedure or a laser procedure, after scar tissue formation. In the preferred embodiment, the temporary sutures are selected such that the sutures dissolve after the formation of the scar tissue bleb. The sutures can be absorbed at any time postoperatively from 1 day up to 8 weeks. Preferably, the sutures are dissolved in 1 to 6 weeks postoperatively. In the preferred embodiment, the dissolving sutures are 8-O Vicryl. As illustrated in FIG. 8, after the bleb 52 forms, the temporary sutures are removed or absorbed by the body, the fluid pressure in the cupped cavity 82 pushes the plate 38 off the surface of the sclera 14 and the seal formed by the sealing surface 69 of the sloped wall 66 against the sclera 14 is broken. The bleb 52 eventually fills with fluid and the seton 38 floats within the fluid in the bleb 52 and maintains the bleb shape. In a preferred embodiment, permanent sutures are utilized in the suture holes 78, 80 on the plate 38 to keep the intermediate end 81 of the seton 38 tethered to the sclera 14 thus preventing the plate 14 from impinging on the eye socket and other tissues in the eye 12 or from extruding. Preferably, with the intermediate end 81 of the plate 38 permanently sutured to the sclera 14, a rearward end 84 of the plate 38 pivots off of the sclera 14. In one embodiment, the tethered plate 38 acts like a leaflet valve. Once the o-ring type seal of the wall 66 is broken, patent flow between the second region 43 of the eye 12, such as the bleb 52, and the first region 42 of the eye 12, such as the anterior chamber 30, is maintained.

Figure 9A:
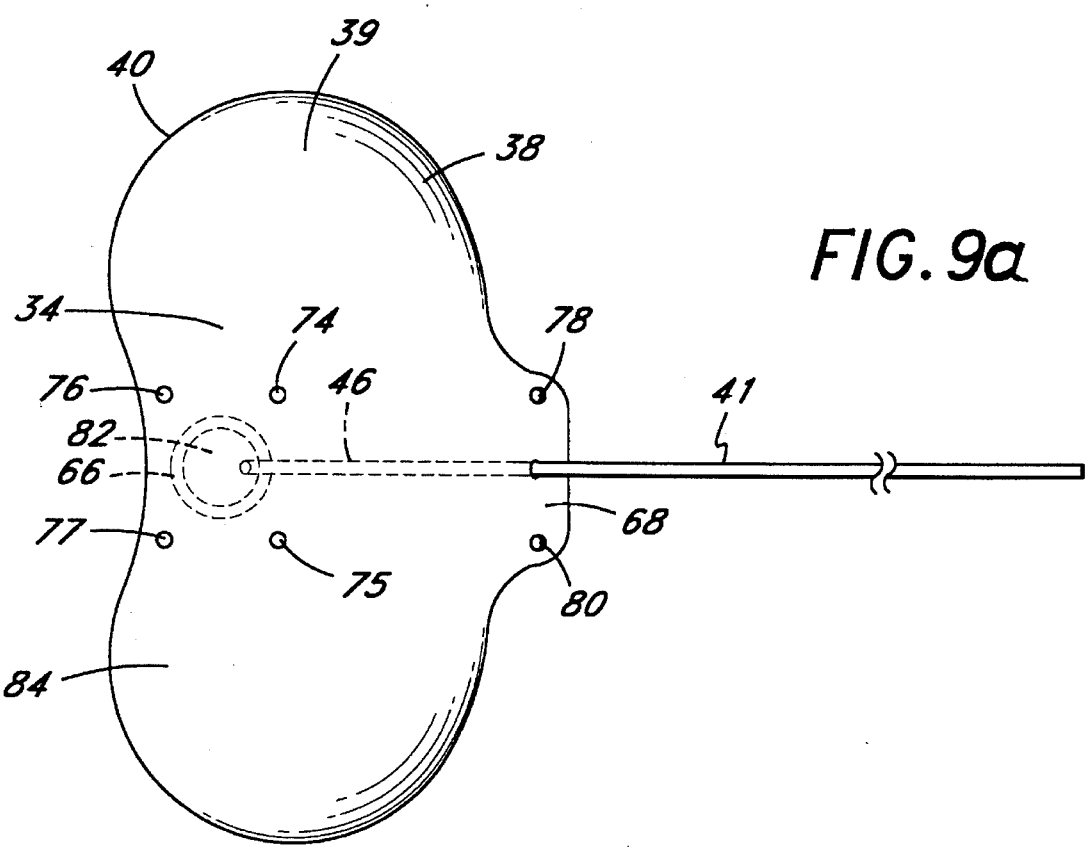
FIG. 9a shows a perspective view of a first configuration of the implant of FIG. 5.
Figure 9B:
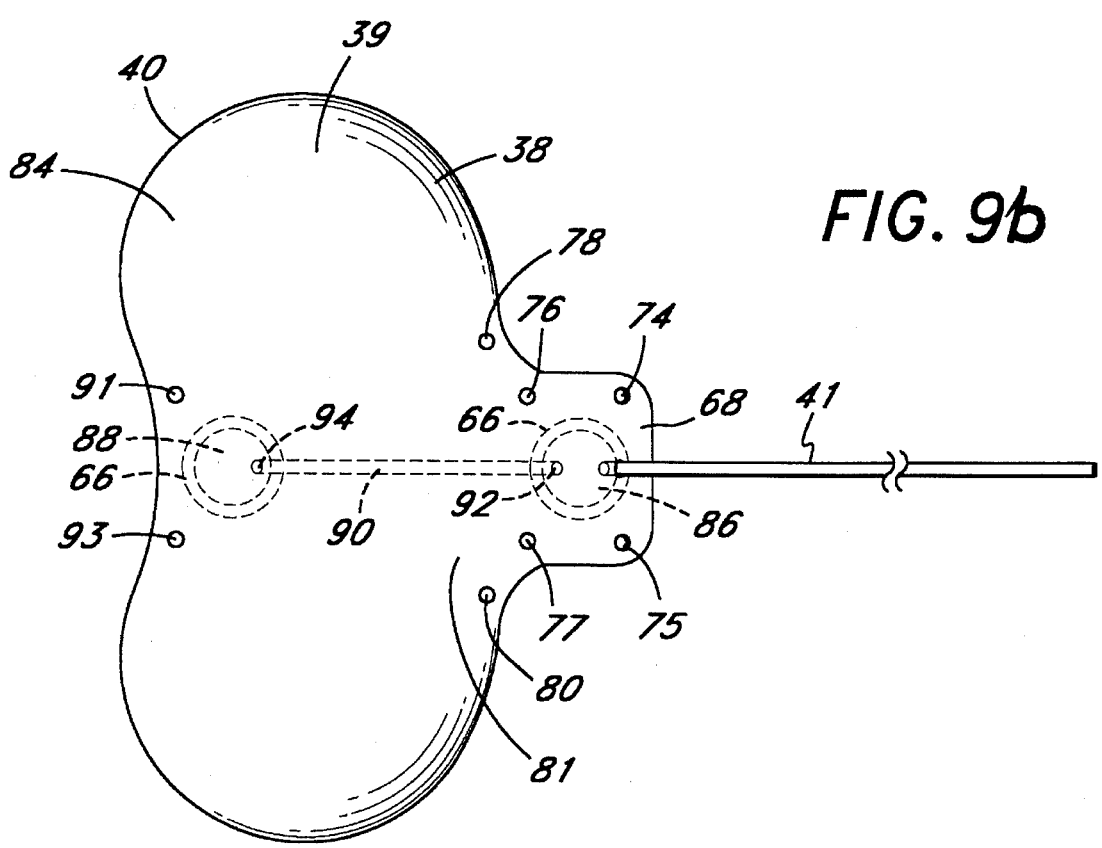
FIG. 9b shows a perspective view of a second configuration of the implant of FIG. 5.
Figure 9C:
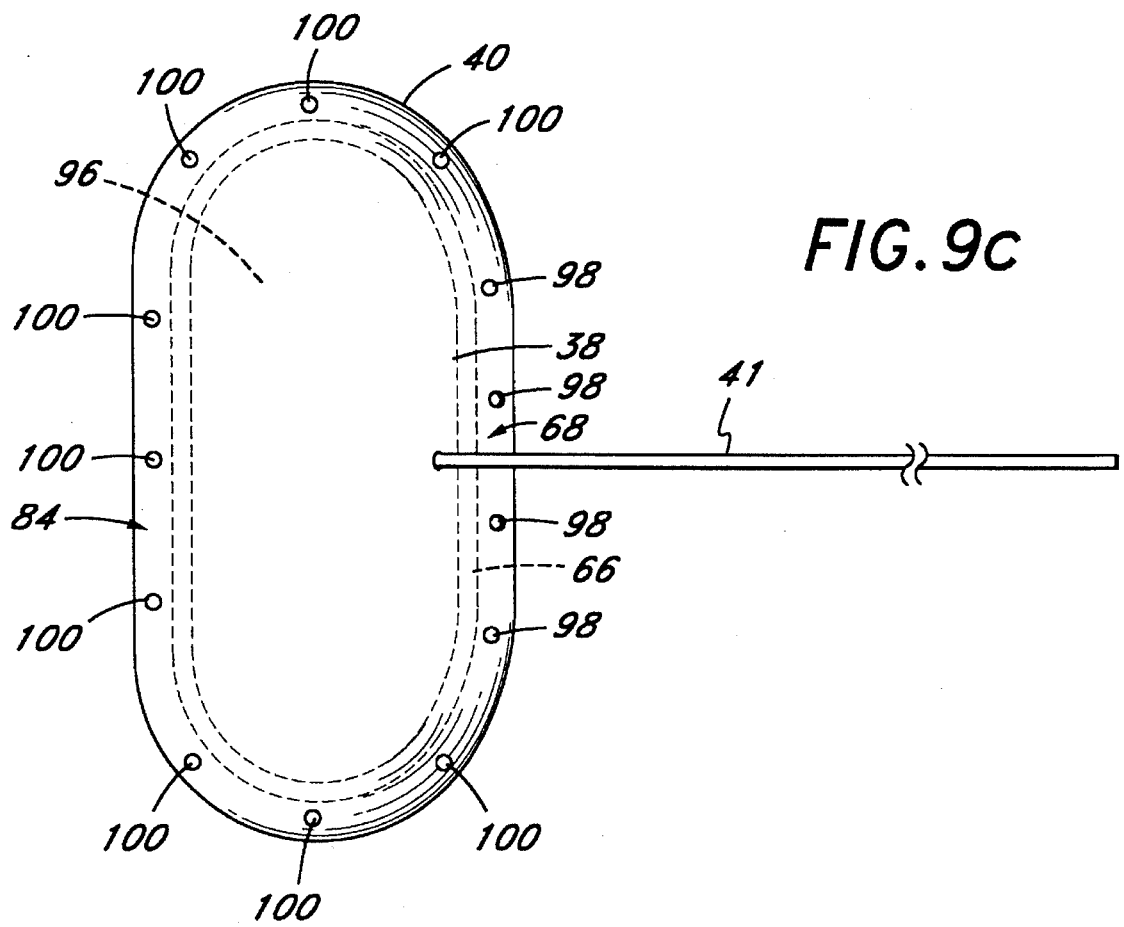
FIG. 9c shows a perspective view of a third configuration of the implant of FIG. 5.

As shown in FIGS. 9a through 9c, a variety of configurations of the sloped wall 66 are possible. Although four configurations are illustrated, one skilled in the art will recognize that various other embodiments could be constructed. In the embodiment illustrated in FIG. 9a, the concave cavity 82 formed by the sloped wall 66 and the second surface 40 of the plate 38 is located in the rearward end 84 of the plate 38. In this embodiment, the tube 41 is attached along the second surface 40 of the plate 38. The tube 41 preferably enters the cavity 82 through a hole (not shown) in the sloped wall 66. The first end 46 of the tube 41 is open to the cupped cavity 82 formed by the sloped wall 66 and the second surface 40 of the plate 38. In this embodiment, the second plurality of suture holes 78–80 are located on the perimeter of the forward portion 68 of the plate 38, while the first plurality of suture holes 74–77 are located on a rearward portion 84 of the plate 38 surrounding the sloped wall 66. Preferably, the plate 38 is attached to the sclera by temporary sutures in suture holes 74–77 and nonabsorbable sutures in the suture holes 78, 80. Preferably, after bleb formation, the temporary sutures in the rearward portion 84 of the plate 38 dissolve and the rearward portion 68 of the plate 38 floats in the bleb while the forward portion of the plate 38 remains attached to the sclera.

In the embodiment of FIG. 9b, a plurality of cavities defined by the sloped walls 66 are formed on the second surface 40 of the plate 38. First 86 and second 88 cavities are connected by a second flexible elastomeric connection tube 90. Preferably, the first end 46 of the drainage tube 41 is open to the first cavity 86. A first end 92 of the connection tube 90 is open to a hole in the first cavity 86. A second end 94 of the connection tube 90 is open to a hole in the second cavity 88. Once both the first 86 and second 88 cavities are filled with aqueous fluid, the fluid pressure in the cavities 86, 88 prevents additional fluid from draining from the anterior chamber 30 of the eye 12. In this embodiment, a third plurality of suture holes 91, 93 are located on the perimeter of the rearward portion 84 of the plate 38. The plate 38 is attached to the sclera by temporary sutures in the first and third plurality of suture holes 74–77 and 91, 93 and nonabsorbable sutures in the second plurality of suture holes 78, 80. Preferably, after bleb formation, the temporary sutures are absorbed by the body, or alternatively removed, and the rearward portion 84 and a portion of the forward portion 68 of the plate 38 float while the intermediate portion 81 of the plate 38 remains attached to the sclera.

In the embodiment of FIG. 9c, one large cavity 96 is formed below substantially the entire second surface 40 of the plate 38 by the addition of the sloped wall 66 around the entire perimeter of the second surface 40 of the plate 38. Permanent sutures are utilized in the suture holes 98 to affix the forward end 68 of the plate 38 to the sclera. A plurality of suture holes 100 are evenly dispersed around the remaining perimeter of the plate 38. Temporary sutures are used in suture holes 100 to temporarily seal the majority of the perimeter of the plate 33. When the temporary sutures 100 dissolve or alternatively are removed, the rearward portion 84 of the plate 38 lifts off of the sclera 14 to enable patent flow of the aqueous humor from the first region 42 of the eye 12 into the bleb 52.

Figure 9D:
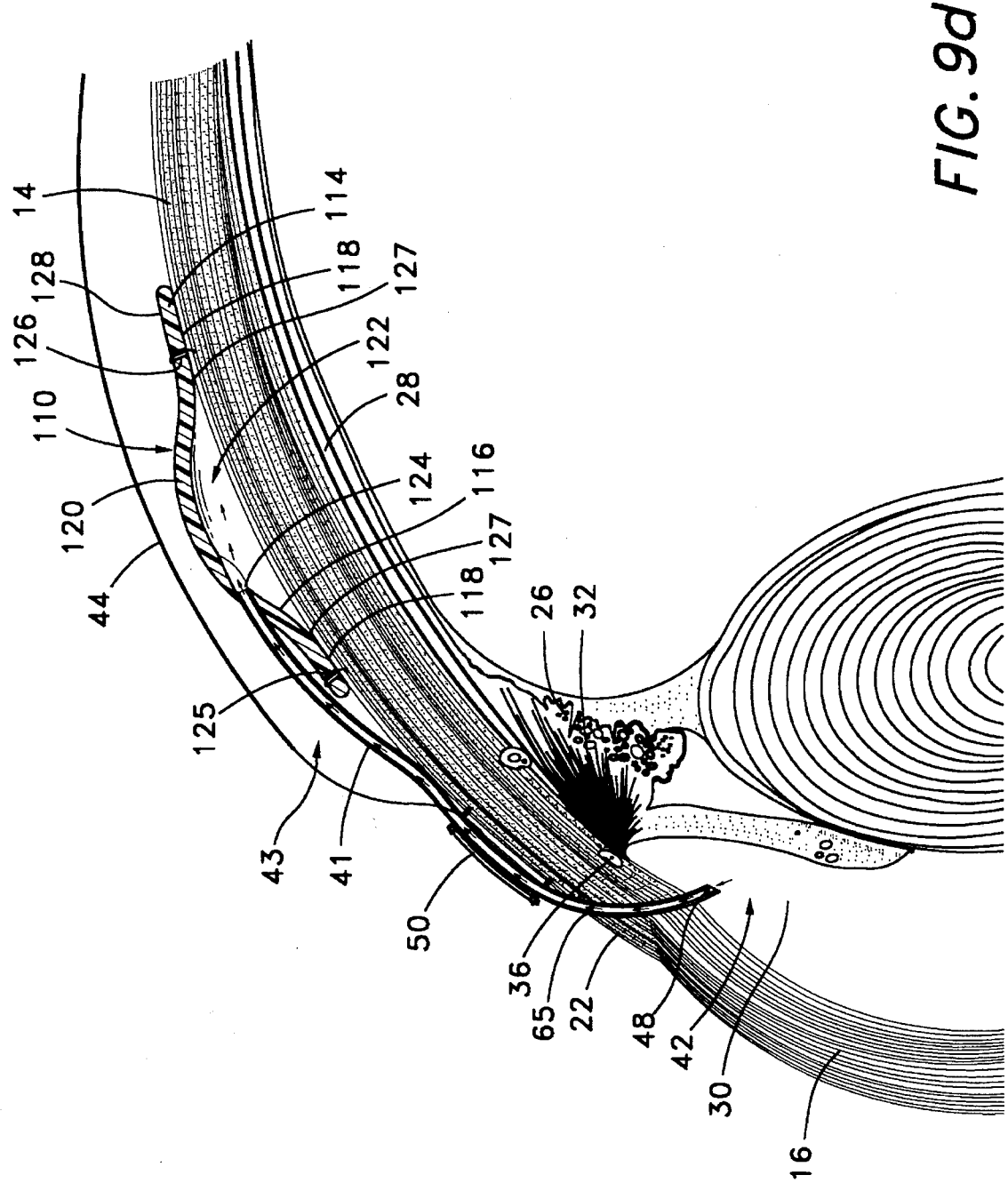
FIG. 9d is a cross-sectional view illustrating another configuration of the implant of FIG. 5 implanted in the eye immediately after surgery.
Figure 9E:
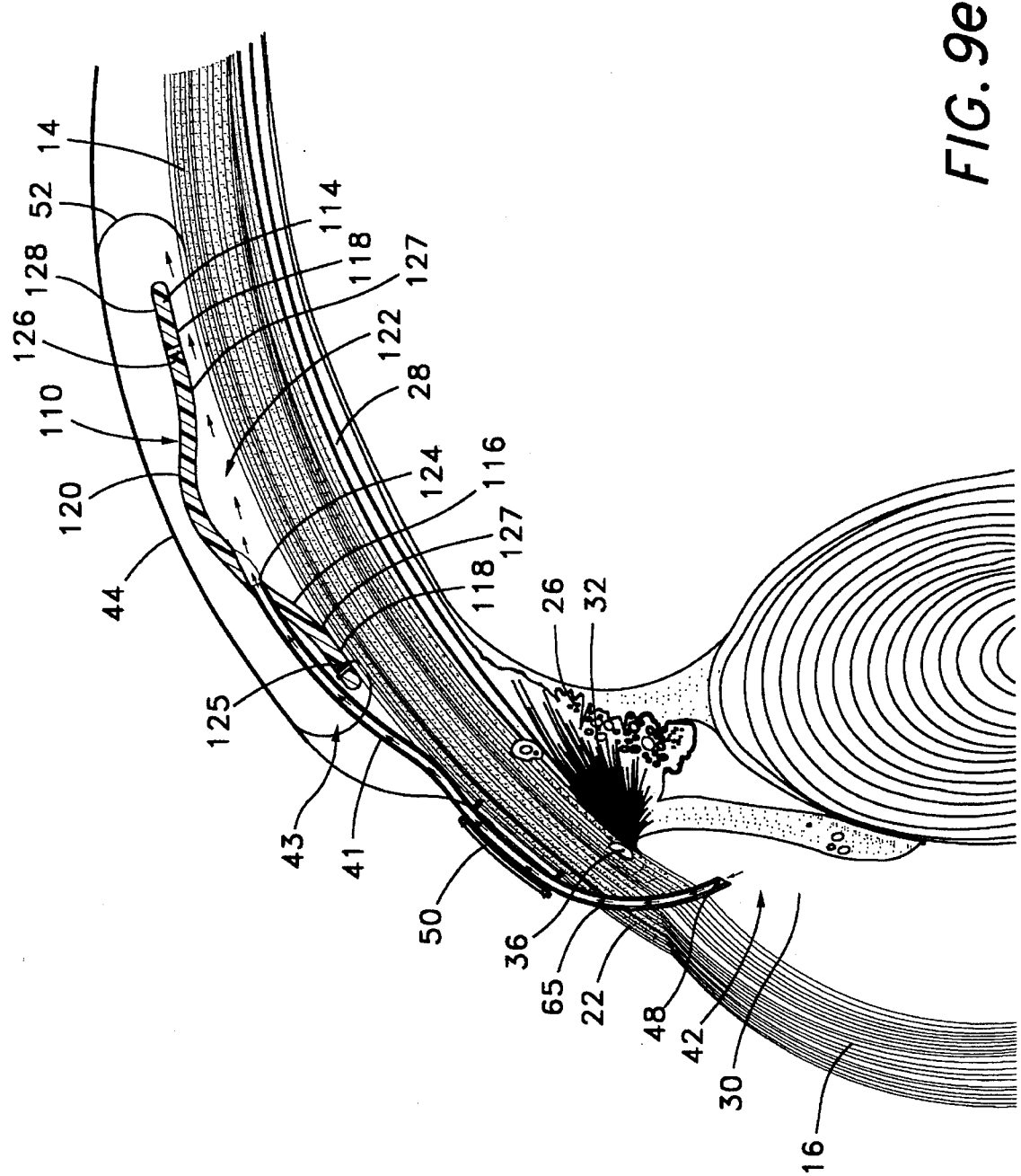
FIG. 9e is a cross-sectional view of the implant of FIG. 9d implanted in the eye after bleb formation occurs.

In the embodiment of FIG. 9d, the shape of the implant 110 is modified to form a cavity 112 within the plate, or seton, 114, rather than including a sloped wall extending from a second surface 116 of the plate 114. The plate 114 preferably is spherically shaped to match the convex anatomy of the eye and has a matching surface 118 around the perimeter of the concave second surface 116 of the plate 114. In a center portion 120 of the plate 114, the plate 114 is shaped such that a hemispherical cupped concave cavity 122 is formed around an opening 124 of the tube 41 in the second surface 116 of the plate 114. In an alternate embodiment (not shown), the plate 114 does not have to include a hemispherical concave cavity 122 formed in the plate 114. Rather, since the plate 114 is pliable, the plate 114 bends to accommodate the physical anatomical convex shape of the patient's eye 12 such that the matching surface 118 around the perimeter of plate is flush with the surface of the sclera 14. A permanent suture is used in suture hole 125 and a temporary suture is used in suture hole 126 to hold the sealing surface 127 of the seton 114 against the surface of the sclera 14. A sealing surface 127 on the matching surface 118 of the plate is formed against the surface of the sclera 14 which temporarily occludes the flow of the aqueous out of the cavity 122. In the embodiment of the platen 114 where a physical cavity 122 is not formed in the plate, the pliable nature of the sutured plate 114 will naturally form a cavity 122 of sufficient size to hold the desired amount of fluid. As illustrated in FIG. 9e, when the temporary suture in suture hole 126 is removed or absorbed by the body, a rearward portion 128 of the seton 114 moves away from the sclera 14 breaking the s:al of the sealing surface 127 against the sclera 14, so that non-valved patent flow of the aqueous can occur.

Figure 10:
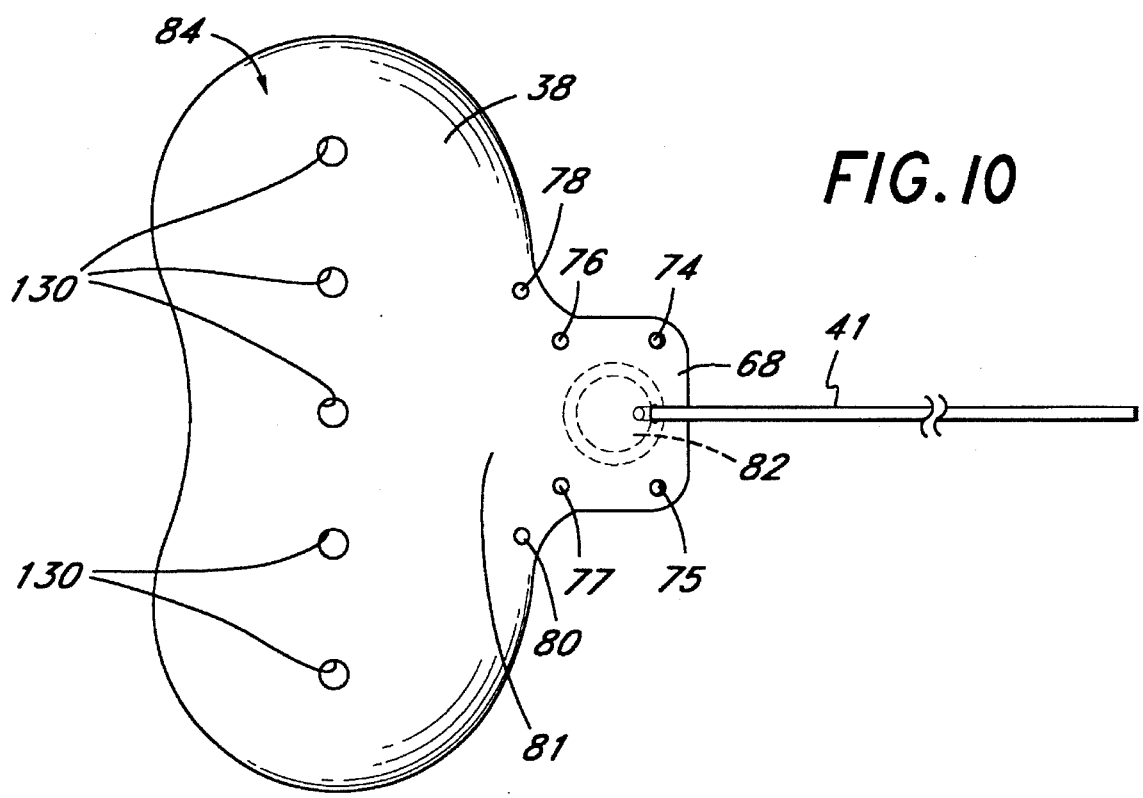
FIG. 10 is a perspective view of an additional alternative embodiment of the implant of the present invention.

Another alternative embodiment of the present invention is illustrated in FIG. 10 which incorporates a plurality of holes, sometimes referred to as fenestrations, 130 in the rearward portion 84 of the plate 38 which does not contain the cavity 82. As illustrated in FIG. 10, the plate 38 has essentially the same shape as the embodiments illustrated in FIGS. 5-6, with the addition of a plurality of aligned holes 130 in the rearward portion 84 of the plate 38. The holes 130 do not interfere with the sealed cavity 82 in the forward portion 68 of the plate 38. However, in the preferred embodiment, once the sutures in the first plurality of suture holes 74-77 around the sealed cavity 82 or the second plurality of suture holes 78, 80 dissolve or are removed and the rearward end 84 of the plate 38 is able to float within the bleb, each of the holes 130 will form a dimple in the bleb by permitting scar tissue growth through each of the holes 130. The overall height of the bleb will be significantly decreased in both the upper and lower directions as the bleb is pulled towards the plate 38 by the growth of scar tissue through each of the holes 130. Preferably, the holes 130 are between 50 microns and 10 mm in diameter. As the number of holes 130 in the plate 38 increases, preferably the diameter of the holes 130 decreases proportionally, but will remain within the above range of preferable diameters. As the number of holes 130 increase in the seton 38, the number of dimples in the resulting drainage bleb will increase proportionately until the horizontal area of the plate 38 and the diameter of the holes 130 limit the addition of the other holes 130.

Although the invention has been described with reference to specific embodiments, the description is intended to be illustrative of the invention and is not intended to be limiting. Various modifications and applications may occur to those skilled in the art without departing from the true spirit and scope of the invention as defined in the appended claims.

What is claimed is:

1. An implant for draining aqueous fluid from a first region of an eye to a second region of said eye which includes the sclera, comprising:

an elastomeric plate, having first and second surfaces to conform to the second region of the eye;

a drainage tube attached to said plate, said drainage tube comprising a first end and a second end, wherein said first end opens onto said second surface of said elastomeric plate and said second end is in communication with said first region of said eye; and a temporary seal member on said second surface of said elastomeric plate for sealing against said sclera in said second region of said eye to temporarily restrict fluid communication between said first region and said second region of said eye.

2. The implant defined in claim 1, wherein said temporary seal member forms an annular ring around said second end of said drainage tube on said second surface of said elastomeric plate.

3. The implant defined in claim 2, wherein said annular ring and said second surface of said plate forms a cup shaped cavity.

4. The implant as defined in claim 1, further including a first plurality of holes and a second plurality of holes in said elastomeric plate, wherein said first plurality of holes provide a first plurality of suture locations and said second plurality of holes provide a second plurality of suture locations to attach said elastomeric plate to said eye.

5. The implant as defined in claim 4, wherein said first plurality of holes provides a first plurality of suture locations to temporarily attach said plate to said eye utilizing absorbable sutures and said second plurality of holes provides a second plurality of suture locations to attach said plate to said eye utilizing nonabsorbable sutures.

6. The implant as defined in claim 4, further including a third plurality of holes in said elastomeric plate, wherein said third plurality of holes provide a third plurality of suture locations to attach said elastomeric plate to said eye.

7. The implant as defined in claim 1, wherein said elastomeric plate additionally comprises a plurality of holes in a rearward portion of said elastomeric plate to enable scar tissue to grow through said holes.

8. The implant as defined in claim 1, wherein the surface area of the elastomeric plate is approximately 100 to 600 $mm^2$.

9. The implant as defined in claim 1, wherein said elastomeric plate is made from silicone.

10. An implant for draining aqueous fluid from a first region of an eye to a second region of said eye, comprising:

a seton, having first and second surfaces, wherein said second surface is concave to conform to the convex surface of the second region of said eye;

a cupped chamber on said second surface of said seton, wherein said cupped chamber is configured to form a temporary seal against the convex surface of the second region of said eye; and an elastomeric drainage tube attached to said seton, said drainage tube comprising a first end and a second end, wherein said first end is open to said cupped shaped chamber and said second end is in communication with said first region of said eye.

11. A method of treating a build up of aqueous fluid in an eye utilizing an implant, said implant comprising an elastomeric plate having first and second surfaces and an elastomeric drainage tube having first and second ends, said plate having a sealing surface on said second surface of said plate, said first end of said drainage tube is open to said second surface and said second end of said drainage tube open to an anterior chamber of the eye, said method comprising the steps of:

temporarily attaching said sealing surface to the sclera of the eye to form a seal against said sclera; and thereafter releasing the seal between said sealing surface and the sclera.

12. A method of treating glaucoma in an eye utilizing an implant, said implant comprising an elastomeric plate having first and second surfaces and an elastomeric drainage tube, wherein a first end of said elastomeric drainage tube is open to said second surface of said plate, said plate having a sloped wall extending from said second surface of said plate surrounding said opening of said drainage tube to said second surface of said plate, said plate having a first and second plurality of suture holes, said method comprising the steps of:

positioning said plate over a sclera of said eye beneath Tenon's capsule, such that said sloped wall forms a sealed cavity in combination with the second surface of said plate and said sclera;

suturing said plate to said sclera utilizing temporary sutures in said second plurality of suture holes;

positioning a second end of said drainage tube within the anterior chamber of said eye;

providing temporary fluid communication between said anterior chamber and said sealed cavity while a scar tissue bleb forms around said implant; and providing patent fluid communication between said anterior chamber and said scar tissue bleb after said temporary sutures are removed.

13. A method of treating glaucoma as defined in claim 12 wherein said temporary sutures are absorbed by the body.

14. A method of treating glaucoma as defined in claim 12 additionally comprising the step of suturing said plate to said sclera utilizing nonabsorbable sutures in said first plurality of suture holes.

15. An apparatus which drains fluid from a glaucoma eye to a drainage location within a patient but prevents dangerously low post-operative pressure in the eye, comprising an implant having a flexible surface, said implant having:

a first portion on the surface of said implant which is configured to form a first small confined reservoir on the sclera in said drainage location immediately after surgery; and a second portion on the surface of said implant which is configured to form a second larger confined reservoir on the sclera in said drainage location only after the passage of a delay period after surgery.

16. A method of draining fluid from a glaucoma eye, comprising:

during surgery, forming a fluid receiving chamber on the sclera of said eye;

sealing off a first portion of said fluid receiving chamber;

immediately after surgery, draining fluid to said first portion of said fluid receiving chamber; and after a delay period after surgery, permitting fluid to drain to a second portion of said fluid receiving chamber which is larger than said first portion.

17. A method of reducing the pressure in a glaucoma eye, comprising:

creating a first sealed drainage region on the sclera of said eye;

draining fluid from said eye into only said first region of the sclera during the immediate post-operative period; and draining fluid from said eye into a second region of the sclera larger than said first region, during a later post-operative period.

* * * * *